US007625585B2

(12) United States Patent
Sessions et al.

(10) Patent No.: US 7,625,585 B2
(45) Date of Patent: Dec. 1, 2009

(54) METHOD OF ATTENUATING NEUROGENIC BRUISE FORMATION

(75) Inventors: Robert W. Sessions, Burr Ridge, IL (US); Alan R. Kahn, Minneapolis, MN (US)

(73) Assignee: Sessions Pharmaceuticals Inc., Burr Ridge, IL (US)

( * ) Notice: Subject to any disclaimer, the term of this patent is extended or adjusted under 35 U.S.C. 154(b) by 188 days.

(21) Appl. No.: 11/440,550

(22) Filed: May 25, 2006

(65) Prior Publication Data
US 2006/0210529 A1 Sep. 21, 2006

Related U.S. Application Data

(60) Continuation of application No. 10/175,119, filed on Jun. 19, 2002, now Pat. No. 7,078,056, which is a continuation of application No. 09/789,275, filed on Feb. 20, 2001, now Pat. No. 6,447,802, which is a division of application No. 09/326,836, filed on Jun. 7, 1999, now Pat. No. 6,451,301.

(60) Provisional application No. 60/088,424, filed on Jun. 8, 1998.

(51) Int. Cl.
*A61K 9/14* (2006.01)
(52) U.S. Cl. .................. 424/484; 424/485; 424/486; 424/78.02; 424/78.06; 424/78.05
(58) Field of Classification Search ............... None
See application file for complete search history.

(56) References Cited

U.S. PATENT DOCUMENTS

| 4,192,868 | A | 3/1980 | Tronchet et al. |
| 5,064,653 | A | 11/1991 | Sessions et al. |
| 5,065,752 | A | 11/1991 | Sessions et al. |
| 5,667,773 | A | 9/1997 | Farrar et al. |
| 6,447,802 | B2 | 9/2002 | Sessions et al. |
| 6,451,301 | B1 | 9/2002 | Sessions et al. |
| 7,078,056 | B2 * | 7/2006 | Sessions et al. ............ 424/484 |
| 2002/0182230 | A1 | 12/2002 | Sessions et al. |

FOREIGN PATENT DOCUMENTS

| EP | 335 669 A2 | 10/1989 |
| EP | 424 164 A2 | 4/1991 |

OTHER PUBLICATIONS

Bessou. et al., J. of Neurophysiology, 32, 1025-43 (1969).
Bonica, "Pain Research and Therapy: Recent Advances and Future Needs" 1-22, in *Advances in Pain Research and Therapy*, vol. 6, Kruger & Liebeskind, eds. (Raven Press, New York (1984)).
Brain, et al., *Nature*, 313, 54-56 (1985).
Blackman, et al., *Diabetes Care*, 17(4) 322-5 (1994).
Blackshaw, et al., *J. Physiol*. 326, 251-260 (1982).
Colpaert, et al., *Life Sci.*, 32, 1827-1834 (1983).
Dodd, et al., "Neurotransmitters and Neuronal Markers at Sensory Synapses in the Dorsal Horn" 105-121, in *Advances in Pain Research and Therapy*, vol. 6, Kruger & Liebeskind, eds. (Raven Press, New York (1984)).
Dubner, et al., "Neural Circuitry Mediating Nociception in the Medullary and Spinal Dorsal Horns" 151-166, in *Advances in Pain Research and Therapy*, vol. 6, Kruger & Liebeskind, eds. (Raven Press, New York (1984)).
Dubner, et al., *Ann. Rev. Neurosci.*, 6, 381-418 (1983).
Duggan, "Inhibition in the Spinal Cord: Its Role in the Response to Injury" 123-134, in *Advances in Pain Research and Therapy*, vol. 6, Kruger & Liebeskind, eds. (Raven Press, New York (1984)).
Fessard, et al., "Tentative Explanation of the Special Role Played by the Areas of Paleospinothalamic Projection in Patients with Deafferentation Pain Syndromes" 167-182, in *Advances in Pain Research and Therapy*, vol. 6, Kruger & Liebeskind, eds. (Raven Press, New York (1984)).
Fields, "Brainstem Mechanisms of Pain Modulation" 241-252, in *Advances in Pain Research and Therapy*, vol. 6, Kruger & Liebeskind, eds. (Raven Press, New York (1984)).
Fowler, et al., *Health Evaluation*, 35 35-44 (1991).
Gamse, et al., *Eur. J. Pharmacol*, 114, 61-66 (1985).
Hanesch, *Prog. Brain Res.*, 113, 299-317 (1996).
Iggo, et al., "Sensory Mechanisms in Arthritic Rat Joints" 83-93, in *Advances in Pain Research and Therapy*, vol. 6, Kruger & Liebeskind, eds. (Raven Press, New York (1984)).
Jancso, et al., *Br. J. Pharmac. Chemother*, 31, 138-151 (1967).
Johansen, et al., *J. Comparative Neurology*, 226, 263-273 (1984).
Katz, *J. Amer. Med.*, 101, 54S-63S (1996).
Kumazawa, *Prog. Brain Res.*, 113, 3-18 (1996).
LaMotte, "Cutaneous Nociceptors and Pain Sensation in Normal and Hyperalgesic Skin" 69-82, in *Advances in Pain Research and Therapy*, vol. 6, Kruger & Liebeskind, eds. (Raven Press, New York (1984)).
Lawson, *Prog. Brain Res.*, 113 369-86 (1996).
Levine, et al., *Science*, 226, 547-9 (1984).
Levine, et al., *J. Immunol.*, 135(2), 843S-847S (1985).
Lewis, et al., "Neural, Neurochemical, and Hormonal Bases of Stress-Induced Analgesia" 277-288, in *Advances in Pain Research and Therapy*, vol. 6, Kruger & Liebeskind, eds. (Raven Press, New York (1984)).
Lewis, Chap. 5, 67-80 in "*The Blood Vessels of the Human Skin and Their Responses*" (Shaw & Sons, London (1927)).
Lin, et al., *J. Amer. Physio. Soc.*, 2602-2611 (1999).
Mayer, et al., "Multiple Endogenous Opiate and Nonopiate Analgesia Systems" 253-276, in *Advances in Pain Research and Therapy*, vol. 6, Kruger & Liebeskind, eds. (Raven Press, New York (1984)).

(Continued)

*Primary Examiner*—Susan C Hoffman
(74) *Attorney, Agent, or Firm*—Leydig,, Voit & Mayer, Ltd.

(57) ABSTRACT

The present invention provides a method of attenuating the formation or reducing the severity of a neurogenic bruise in the tissue of a patient via applying a composition comprising a hydrophilic foam substrate and a polymeric hydrophilic agent to a portion of the surface of the skin in an amount and at a location sufficient to attenuate formation of or reduce the severity of bruising.

2 Claims, No Drawings

OTHER PUBLICATIONS

Melzack, "Neuropsychological Basis of Pain Measurement" 323-339, in *Advances in Pain Research and Therapy*, vol. 6, Kruger & Liebeskind, eds. (Raven Press. New York (1984)).

Ochoa, "Peripheral Unmyelinated Units in Man: Structure, Function, Disorder, and Role in Sensation" 53-68, in *Advances in Pain Research and Therapy*, vol. 6, Kruger & Liebeskind, eds. (Raven Press, New York (1984)).

Pastor, et al., *J. Neurophysiol.*, 75, 2268-79 (1996).

Perl, "Characterization of Nociceptors and Their Activiation of Neurons in the Superficial Dorsal Horn: First Steps for the Sensation of Pain" 23-51, in *Advances in Pain Research and Therapy*, vol. 6, Kruger & Liebeskind, (Raven Press, New York (1984)).

Price, "Roles of Psychophysics, Neuroscience and Experiential Analysis in the Study of Pain" 341-355, in *Advances in Pain Research and Therapy*, vol. 6, Kruger & Liebeskind, eds. (Raven Press, New York (1984)).

Ralston, III, "Synaptic Organization of Spinothalamic Tract Projections to the Thalamus, with Special Reference to Pain" 183-195, in *Advances in Pain Research and Therapy*, vol. 6, Kruger & Liebeskind, eds. (Raven Press, New York (1984)).

Reeh, et al., *Brain Res.*, 384, 42-50 (1986).

Rivot, et al., "Involvement of Serotonin in Both Morphine and Stimulation-Produced Analgesia: Electrochemical and Biochemical Approaches" 135-150, in *Advances in Pain Research and Therapy*, vol. 6, Kruger & Liebeskind, eds. (Raven Press. New York (1984)).

Treede. *Neurosci. Let.*, 141, 169-172 (1992).

Vierck, et al., "Guidelines for Assessing Pain Reactions and Pain Modulation in Laboratory Animal Subjects" 305-322, in *Advances in Pain Research and Therapy*, vol. 6, Kruger & Liebeskind, eds. (Raven Press, New York (1984).

Wall, "Mechanisms of Acute and Chronic Pain" 95-104, in *Advances in Pain Research and Therapy*, vol. 6, Kruger & Liebeskind, eds. (Raven Press, New York (1984)).

Weihe, et al., *Ann. N.Y. Acad. Sci.*, 632, 283-95 (1991).

White, et al., *Brain Res.*, 336, 27-31 (1985).

Willis, "Modulation of Primate Spinothalamic Tract Discharges" 217-240, in *Advances in Pain Research and Therapy*, vol. 6, Kruger & Liebeskind, eds. Raven Press, New York (1984)).

Yaksh, "Multiple Spinal Opiate Receptor Systems in Analgesia" 197-215, in *Advances in Pain Research and Therapy*, vol. 6, Kruger & Liebeskind, eds. (Raven Press, New York (1984)).

Young, et al., "Electrical Stimulation of the Brain in the Treatment of Chronic Pain in Main" 289-303, in *Advances in Pain Research and Therapy*, vol. 6, Kruger & Liebeskind, eds. (Raven Press, New York (1984)).

Carr et al., "Clinical Evaluation of a Polymeric Membrane Dressing in the Treatment of Pressure Ulcers", *Decubitus*, vol. 3 (3), (1990).

Carr et al., *Wounds*, vol. 1 (1), 53-61 (1989).

Cunningham at al., "Wound Healing After Lancing the Skin," *Wounds: A Compendium of Clinical Research and Practice*, 12 (5), 131-137 (2000).

David et al., "Tissue damage and repair," *Wound Management A Comprehensive Guide to Dressing and Healing*, Springhouse Corporation, Springhouse, PA, pp. 1-21 (1986).

Sussman, "Assessment of the Skin and Wound," *Wound Care A Collaborative Practice Manual for Physical Therapists and Nurses*, Aspen Publishers, Inc., Gaithersburg, Maryland, Chapter 3, pp. 49-82 (1998).

Vertanen at al., An automatic incision device for obtaining blood samples from the heels of preterm infants causes less damage than a conventional manual lancet, *Arch Dis Child Fetal Neonatal Ed.* 2001, 84(1):F53-5.

International Search Report, PCT Pub. No. WO 99/64081A1 (Sessions et al.; PCT/US00/12738) (5 pages, issued Sep. 28, 1999).

* cited by examiner

METHOD OF ATTENUATING NEUROGENIC BRUISE FORMATION

CROSS-REFERENCE TO RELATED APPLICATIONS

This is continuation application of U.S. patent application Ser. No. 10/175,119, filed on Jun. 19, 2002; now U.S. Pat. No. 7,078,056, which is a continuation of U.S. patent application Ser. No. 09/789,275, now U.S. Pat. No. 6,447,802, filed on Feb. 20, 2001; which is a divisional application of U.S. patent application Ser. No. 09/326,836, now U.S. Pat. No. 6,451,301, filed Jun. 7, 1999; which claims priority to U.S. Provisional Patent Application No. 60/088,424, filed Jun. 8, 1998; all of which are hereby incorporated by reference, in their entirety, into the current application.

TECHNICAL FIELD OF THE INVENTION

The present invention relates to analgesic and antinociceptive methods.

BACKGROUND OF THE INVENTION

Peripheral nociceptors are neurons primarily responsible for responding to noxious stimuli giving rise to pain. Most nociceptors are non-myelinated C-fibers, and they are among the smallest diameter of mammalian neurons (see, e.g., Chapter 48 in *Textbook of Medical Physiology*, 7$^{th}$ Ed., Guyton, (W.B. Saunders, Co., 1986)). C-fibers are peptidergic neurons releasing tachykinins (notably Substance P and neurokinins), calcitonin gene-related peptide (CGRP), and other neuroactive peptides. The peripheral nociceptor termini (the neurites responsible for initial transduction of noxious stimulus), lie throughout the body in cutaneous, subcutaneous and visceral organs and tissues (Dubner et al., *Ann. Rev. Neurosci.*, 6, 381-418 (1983); Coggshall et al., *Brain Res.*, 272, 185-88 (1983)). Generally, the peripheral termini of nociceptors are loosely arrayed into networks of neurites able to interact with each other as well as react to endogenous and exogenous environmental noxious stimuli. Such networks represent the branched termini of neurites lying within nerves whose somas are within the paired dorsal root ganglia (DRG) lying to each side of the spinal column in a semisegmental array. Afferent nociceptor neurites run from the DRG to innervate the spinal substantia gelatinosa. Generally, spinal nociceptive innervation is via synapses with projection neurons ascending into the contralateral spinothalamic tract, through the thalamus, and ultimately to the cerebral cortex (Fields, 479-86 in *Advances in Pain Research and Therapy*, Fields et al., eds. (Raven Press, New York, 1985); Jessell et al., 384-99 in *Principles of Neural Science*, 3d. ed., Kandel et al., eds. (Elsevier, New York, 1991)).

Nociceptive neurons play a dual role in the transduction of noxious stimuli. In one mode, nociceptors mediate local physiological response to such stimuli. Roughly 90% of the substance P produced in nociceptor somas is transported to the peripheral nociceptor termini (Levine et al., *J Immunol.*, 135, 843S-47S (1995); Brimjoin et al., *Brain Res.*, 191, 443 (1986)). Upon stimulation, the peripheral nociceptor termini release peptide agents, which mediate a number of physiological responses locally. Peripherally-released substance P and CGRP cause vasodilation, increase vascular permeability, and trigger plasma extravasation of cells in the region of the nerve termini (see, e.g., Gamse et al., *Eur. J Pharmacol*, 114, 61-66 (1985); Brain et al., *Nature*, 313, 54-56 (1985); Reeh et al., *Brain Res.*, 384, 42-50 (1980); Katz et al., *Am. J Med.*, 101, 1A55S-63S (1996)). Additionally, tachykinins effect degranulization of mast cells, which, in turn, release histamine. Thus, antidromic stimulation of nociceptors mediates the characteristic "wheal and flare" reaction, characterized by tissue swelling through the direct action of released substance P as well as indirectly, such as via increased local histamine concentration from mast cells (Katz, supra; Foreman et al., *Agents and Actions*, 13, 105-226 (1983)). Within joints, such swelling is associated with arthritis (Levine et al., *J Immunol*, 135, 843S-47S (1985); Levine et al., *Science*, 226, 547-49 (1984)). Additionally, as mentioned, nociceptor termini are arranged in loose networks. Such networks effect cross-talk and interaction between nociceptor termini. Thus, stimulation of nociceptors effects a positive feedback response on the nociceptors themselves, as substance P sensitizes nociceptors, and as histamine stimulates the nociceptors by reducing their threshold (Lembeck et al., *Trends Neurosci.*, 6, 106-08 (1983); Weihe, *Ann. N.Y Acad. Sci.*, 632, 283-95 (1991)).

Aside from mediating local physiological change to noxious stimuli, the nociceptors transmit signals from the periphery to the central nervous system. The neural pathways primarily innervated by nociceptors are associated with pain sensation. In this regard, the organization of their spinal innervation is important for the overall sensation of pain. Signals received by the aforementioned rising spinal neural pathways represent aggregation or summation of signals received from nociceptors from a given level (or segment) of afferent inputs, whether the nociceptive nerve termini lie in the skin or internal organs. This organization of afferent inputs generally produces a segmental map or "dermatome" representation of skin and internal organs relating to segmental innervation, although some longitudinal cross-talk occurs. Due to this aggregation, signals received from internal organs are often "felt" or experienced as if they originated in the same dermatome as the internal organ (giving rise to phenomena such as "phantom pain" or "referred pain"). A similar arrangement exists for cranial nerves. Thus, there are relatively consistent dermatomal representations of internal organs on the human body surface.

The neuroactive peptides (notably substance P) released by nociceptors at the sites of their synapses in the central nervous system can simultaneously stimulate other innervating nociceptive efferent tennini within the central nervous system. Due to antidromal signal conductance along such nociceptors from the central nervous system, the peripheral termini of nociceptors in areas distant from the situs of the noxious stimuli can be caused to release tachykinins and other peptides. Thus, lateral cross-talk or reflexive input in the spinal column can lead to a nociceptor mediated "neurogenic inflammation" in an area separate from the initial noxious stimulus (e.g., skin on the contralateral side, joints, internal organs, etc.) within the same dermatome (Levine et al., *J Neurosci.*, 5, 1380-85 (1985)). Similarly, nociceptive input from termini lying in a given area of skin can often be "felt" or experienced in a similar locus on the contralateral side of the animal, particularly within the same dermatome.

Considering their dual role in sensing pain and in effecting local responses to nociceptive stimuli, several efforts have focused on blocking or attenuating nociceptor activity. One method of attenuating nociceptor activity is via capsaicin, the active agent of red peppers. Capsaicin acts on C-fibers to deplete them of neuropeptides (Janscó et al., *Naunyn-Schmiedberg Arch. Pharmacol.*, 313, 91-94 (1980)), leading to diminished response to noxious stimuli. Capsaicin can be applied topically, such as in a cream, to the skin, and it will diffuse through the skin to act on the subcutaneous C-fibers.

Using capsaicin to block C-fiber response poses several drawbacks. Notably, the compound can cause degeneration of the C-fibers (Janscó et al., *Br. J Pharmacol.*, 31, 138-51 (1967); Anton et al., *Neurosci. Lett. Supp.*, 22, 31 (1985)). Moreover, capsaicin can irreversibly decrease the amount of substance P in the skin (Gamse et al., *Br. J Pharmacol.*, 68, 207-13 (1980); Reeh et al., *supra.*). Some reports note that the compound must be applied repeatedly to be effective (Zochodne, et al., *J Can. Sci. Neurol.*, 20, 69-72 (1993)). Also, many formulations for topical capsaicin application are incompatible with broken (e.g., wounded) skin. Furthermore, due to its mode of action by depleting the neuropeptides associated with pain, capsaicin application initially leads to acutely heightened pain sensation and inflammation. This acute pain is experienced as an intolerable burning in some patients and renders controlled or blind studies involving capsaicin difficult or impossible (Kost et al., *New Eng. J Med*, 335, 32-42 (1996)).

Another means of affecting the nociceptors is with gold salts. For example, gold salts are effective against progressive joint destruction in patients with arthritis (Gottleib, 796-814 in *Textbook of Rheumatology*, Kelly et al., eds. (W. B. Saunders, Philadephia (1981)). Gold salts reduce swelling and pain through an irreversible neurotoxicity specific for nociceptors (Levine et al., *Arthritis Rheumat.*, 29, 897-901 (1986)). Because gold salts destroy the C-fibers, employing them as therapeutic agents to minimize pain and swelling is suboptimal in many applications.

In view of the foregoing problems, there exists a need for a nontoxic method of attenuating the response of nociceptors to noxious stimuli and mitigating the symptoms thereof. The present invention seeks to overcome these problems by providing a therapeutic method involving the application of a composition comprising a hydrophilic foam substrate, a polymeric hydrophilic agent capable of absorbing water, and a wetting agent to the surface of the skin. In various aspects and protocols, the invention can promote healing and prevent the formation of a bruise in traumatized tissue, attenuate swelling and neurogenic inflammation, reduce the sensation of pain, and mitigate other symptoms associated with activation of the nociceptive system. These aspects of the invention, as well as additional advantages and inventive features, will be apparent from the following description.

DETAILED DESCRIPTION OF THE INVENTION

The present invention concerns a method of treating a patient to attenuate, and in some cases eliminate, symptoms (e.g., pain, inflammation, bruising, etc.) normally caused or potentiated by the activation of the nociceptive system through the use of a composition including at least a hydrophilic foam substrate, a hydrophilic agent capable of absorbing water, and a wetting agent to the surface of the skin. The composition is applied to the surface of the skin in an amount and at a location sufficient to attenuate the response of the nociceptors to noxious stimuli.

A preferred type of foam substrate for use in the inventive method is a highly absorbent hydrophilic polyurethane foam composition, for example, the in situ reaction product of a reactant composition comprising an isocyanate-capped polyether prepolymer. Generally, such prepolymers must be safe for use in the human body, and are preferably capable of foaming in an aqueous system in the absence of a catalyst. On the other hand, such prepolymers should not dissolve in the aqueous liquid. Additionally, it is highly desirable that these prepolymers cure to form a porous cellular foam matrix to enable both absorption of external fluids and carriage of the chosen wetting agent and hydrophylic agent in the composition. The formation of a cellular foam matrix is preferred due to a large volume available not only for absorption but the containment of the other constituents. It is further desirable that the prepolymers be capable of curing in the presence of water, in the absence of catalyst, and at ambient temperature (e.g., about 20° C. to about 30° C., preferably about 25° C.).

Isocyanate-capped polyether prepolymers, such as those disclosed in U.S. Pat. No. 3,903,232 and U.S. Pat. No. 4,137,200, are suitable for use in a hydrophilic polyurethane foam composition. These prepolymers have a defined average isocyanate functionality greater than 2. These prepolymers can be capped with aromatic isocyanates, such as, for example, toluene diisocyanate or methylene diphenyl isocyanate, or with aliphatic isocyanates, such as isophorone diisocyanate.

Isocyanate-capped polyether prepolymers which have been found suitable include prepolymers sold under the trademark HYPOL. Examples include HYPOL FHP 2000, HYPOL FHP 2002, HYPOL FHP 3000, HYPOL FHP 4000, HYPOL FHP 5000, HYPOL X6100 and HYPOL hydrogel. HYPOL 2000, HYPOL 2002 and HYPOL 3000 prepolymers are derived from toluene diisocyanate. FHP 2000 and FHP 2002 both have an equivalent weight (per NCO) of 625, an NCO content of 1.60 meq/g and a specific gravity of 1.19. The viscosity of FHP 2000 is 18,500 cps (Brookfield LVF, #4 Spindle, 12 rpm at 25° C.) and that of FHP 2002 is 20,000. FHP 3000 has an equivalent weight (per NCO) of 425, an NCO content of 2.35 meq/g, a specific gravity of 1.15 and a viscosity (measured as described above) of 10,500. HYPOL hydrogel is likewise derived from toluene diisocyanate. It has an NCO content of 0.5-0.9 meq/g and a viscosity of 10,000 to 12,000 cps at 25° C. The HYPOL FHP 4000 and HYPOL FHP 5000 prepolymers are derived from methylene diisocyanate. FHP 4000 has an equivalent weight (per NCO) of 476, an NCO content of 2.10 meq/g, a Brookfield viscosity (LVF, #4 Spindle, 12 r.p.m. at 25° C.) of 20,000 and specific gravity of 1.17. FHP 5000 has an equivalent weight (per NCO) of 392, an NCO content of 2.55 meq/g, a Brookfield viscosity (measured as for FHP 4000) of 18,000 and a specific gravity of 1.17. HYPOL X6100 has an NCO content of 1.8 meq/grams and a viscosity at 25° C. of 12,000 cps.

Another example of an isocyanate-capped prepolymer suitable for use in a hydrophilic foam composition and derived from toluene diisocyanate is AQUAPOL prepolymer, commercially available from Freeman Chemical Corporation. AQUAPOL prepolymers have an NCO-value of 2.5 to 3.0 and are formed from the reaction of toluene diisocyanate and an organic polyether polyol containing at least 40 percent by weight ethylene oxide adducts as described at Col. 2, lines 3-22 of U.S. Pat. No. 4,517,326.

A further example of an isocyanate-capped prepolymer suitable for use in a hydrophilic foam composition and which is derived from toluene diisocyanate is sold under the trademark TREPOL, and is commercially available from Twin Rivers Engineering. TREPOL prepolymers have an —NCO content of 1.4 meq per gram and a viscosity at 90° C. of 4,700 cps.

The amount of prepolymer in the reactant composition used to prepare the hydrophilic foam composition is not particularly critical, but depends on a number of factors, including the proportion of other components in the reactant composition as will be described in greater detail hereinafter. However, there should be sufficient prepolymer to form a polyurethane foam, to adequately contain the hydrophilic agent and adjuvant (if present). To that end, the ratio of prepolymer to hydrophilic agent should be such that the reactant composition does not degrade or break up into its separate constituents. Furthermore, while there should be sufficient prepolymer to provide integrity to the foam matrix, there should not be so much prepolymer that the resulting polyurethane composition becomes unworkable. In short, and particularly where the final composition is to be applied to the skin, the resulting foam composition is desirably relatively smooth and soft while exhibiting the desired absorbence characteristics so that it does not irritate or otherwise harm the skin. The concentration of prepolymer further depends on its isocyanate functionality and the degree of crosslinking desired in the final foam composition. In general, the greater the isocyanate functionality, the greater the degree of cross-linking in the cured foam matrix. Typically, the reactant composition will comprise from about 20% to about 60% by weight prepolymer. Preferably the reactant composition will comprise from about 45% to about 50% by weight of the prepolymer. Advantageously, the prepolymers can be used alone or in combination.

The composition further includes a hydrophilic agent, which is incorporated into the foam composition to absorb external liquid (e.g., wound exudate, sweat, etc.) and to retain such liquid in the composition. The hydrophilic agent preferably is a highly absorbent polymer, commonly known as a superabsorbent polymer. One measure of polymer absorbency is its fluid uptake capability, well known by those skilled in the art. Hydrophilic agents suitable for use in a hydrophilic foam composition include polymers that are capable of absorbing at least 50 times their weight of water, that is, such agents have a fluid uptake of at least 50 ml/g. Hydrophilic agents having an even higher fluid uptake, such as of at least about 100 ml/g and even higher, that is, at least about 150 ml/g are preferred. Suitable superabsorbent polymers include sodium and aluminum salts of starch grafted copolymers of acrylates and acrylamides and combinations thereof, as well as polyacrylate salts. Of course, other absorbent materials can be used in combination with such highly absorbent polymers, provided the fluid uptake of the overall combination used for the hydrophilic agent is greater than 50 ml/g. Examples of such additives include methylcellulose, guar gum, pectin, karaya gum, chitosan, agar, acacia powder, carrageenan, gelatin and combinations thereof. When such agents are employed, either alone or in combination, the resulting foam composition desirably has the ability to hold at least about 3 times its weight in liquid.

Hydrophilic polymers which have been found suitable for use in the foam composition are commercially available from Grain Processing Corporation. These polymers include a starch-g-poly (2-propenamide-co-2-propenoic acid, mixed sodium and aluminum salt) sold under the trademark WATER LOCK A-222; a starch-graft copolymer of polyacrylic acid and polyacrylamide having the chemical name starch-g-poly (2-propenamide-co-2-propenoic acid, sodium salt), sold under the trademark WATER LOCK A-100; a starch g-poly (2-propenamide-co-2-propenoic acid, sodium salt), sold under the trademark WATER LOCK A-200. Superabsorbent polymers commercially available from Grain Processing Corporation under the trademark WATER LOCK D-212 and WATER LOCK D-242 are likewise suitable. These polymers have the chemical name starch-g-poly (2-propenamide-co-2-propenoic acid, mixed sodium and aluminum salt). The superabsorbent polymer commercially available under the trademark WATER LOCK G-400 is also suitable for use in the making of a hydrophilic foam composition. This superabsorbent polymer can be chemically identified as a poly (2-propenamide-co-2-propenoic acid, sodium salt). Other super absorbent powders suitable for use in a hydrophilic foam composition are sold by Grain Processing Corporation under the trademark WATER LOCK B, C, and H.

Another example of a suitable superabsorbent polymer is poly-2-propenoic acid, sodium salt, sold under the trademark AQUA KEEP J-500 supplied by Sanyo Corp. In addition, super absorbent polymers sold by Arakawa Chemical (USA) Inc. under the trademark ARASORB are suitable. The preferred hydrophilic polymers are WATER LOCK A-100, A-200, A-222 and AQUA KEEP J-500. The hydrophilic polymers can be used alone, or in combination to achieve the desired absorbance characteristics in the foam composition.

The amount of hydrophilic agent used and the type of it, in terms of its fluid uptake, that can be satisfactorily used to make the foam composition is not critical, but is, instead, dependent on the intended application of the composition. The amount of hydrophilic agent should not be so great as to undesirably reduce the strength of the foam composition or result in a loss of polymer from the foam, although some loss of hydrophilic agent can be tolerated without adversely affecting the ability of the foam to absorb external liquid. The amount of hydrophilic agent employed in the reactant composition will also depend on the absorbency of the material used. As previously indicated, it is preferable that a sufficient amount of hydrophilic agent be employed so that the resulting foam composition is capable of absorbing at least about 3 times its weight in external liquid. Typically this can be achieved by including from about 5 wt. % to about 20 wt. % hydrophilic agent in the reactant composition.

The wetting agent should not react with the foam composition or any component of the foam formulation to create difficulties during foam formation or to adversely affect the desired characteristics of the foam composition in use or while being stored. Examples of materials that can be used as the wetting agent, either alone or in admixture, include nonionic surfactants, such as block copolymers of ethylene oxide and propylene oxide sold under the trademark PLURONIC by BASF Wyandotte corporation, ethoxylated sorbitan fatty acid esters, glycerol esters, polyglycerol esters, and silicone fluids. PLURONIC F-68 and L-62 are preferred. As is known, PLURONIC F-68 aids in wound cleansing without causing tissue damage. The use of PLURONIC F-68 is especially preferred because of its cleansing action, particularly because a portion of the surfactant can be released when the foam composition is exposed to the exudate of the wound. Generally, the amount of wetting agent should be from about 1% to about 10% by weight of the reactant composition, preferably from about 5% to about 7% by weight.

In addition to the hydrophilic foam substrate, polymeric hydrophilic agent capable of absorbing water, and wetting agent, the composition can include other ingredients. Indeed, preferably the composition includes at least one adjuvant, such as, for example, mono-, di- and polyhydric alcohols. Preferably such adjuvants are water soluble so that they are miscible with biological fluids, especially those present in the extracellular matrix. It is also highly desirable that the adjuvant be capable of contacting skin without adverse side effects. To that end, it is also preferable that the adjuvant comprise a chemical compound that will have the ability to open the skin pores to achieve a demulcent effect to relieve pain and/or irritation and to achieve an emollient effect to soften the skin and prevent maceration. It is also preferred that the adjuvant be compatible with therapeutic or other agents which may be carried by the composition (e.g., carried by the carrier, the adjuvant, or another component of the composition) for delivery to the situs of application.

Suitable adjuvants include water-soluble alcohols, including monols, diols and polyhydric alcohols and other organic compounds with —OH groups; and mixtures of such alcohols can likewise be used. In general, the molecular weight of the alcohols should be less than about 1000. Examples of monols include ethyl alcohol and isopropyl alcohol. Exemplary of suitable diols are propylene glycol, polyethylene glycol and polypropylene glycol. Exemplary of suitable polyhydric alcohols are glycerin, 1, 2, 4-butanetriol, trimethylolpropane, pentaerythritol and sorbitol. Glycerin is preferred as it has the attributes of a medicament, cosmetic or therapeutic agent.

Prior to curing, the adjuvant can serve as a plasticizer for the reactant foam composition. It extends the curing time of the composition, thereby allowing it to be more thoroughly mixed and formed. Once cured, the foam composition is softened by the adjuvant, allowing the foam to be more pliable and more easily applied to the skin surface or other surface of choice. Additionally, the adjuvant can be somewhat hygroscopic lending further to the hydrophilic nature of the foam composition. The amount of adjuvant included in the reactant composition should preferably be sufficient to impart softness and pliability to the foam composition and be capable of delivering a therapeutic agent or the like, if included, to the environment of application. However, the volume of adjuvant should not be so great as to weaken or gel the composition. Generally, it has been found that the amount of adjuvant in the reactant composition can be up to about 30 wt. % of the reactant composition.

Various additional medicaments, cosmetics and therapeutic agents can be carried within the composition and released to the desired situs. This release allows the transmission of such therapeutic or other agents carried in the composition to the area of application outside the composition, further assisting in the beneficial treatment. Illustrative of therapeutic agents which can be incorporated into the composition are Collasol 2400, Crotein SPA, Cromoist HYA, Crotein CAA and hydrocortisone acetate and polymers with medicinal properties. Illustrative of cosmetic agents which can be incorporated into the composition are European Collagen Complex, Capture Complex Liposomes, Sardo™ bath oil, a hand lotion sold under the trademark Jergens TM, Noxema™ skin cream, Oil of Olay™ BF, Keri™ lotion, polymers with cosmetic properties, Vaseline™ herbal and aloe lotion, Ben Gay™ ointment, Retin-A™ cream, and trans-retinoic acid.

The composition for use in the inventive method can be prepared by any suitable method, for example, as described in U.S. Pat. No. 5,254,301, incorporated herein by reference. Preferably, to effect foaming and the preparation of the composition for use in the inventive method, such method involves the preparation and mixing of an organic phase and an aqueous phase. The organic phase includes the prepolymer and preferably the hydrophilic agent. The aqueous phase includes the wetting agent, the hydrophilic agent (if it is not included in the organic phase), and other desired additives, such as, for example, the adjuvant, dyes or the like to color the resulting foam, medicaments, etc. To prepare the foam, the organic phase and aqueous phase are mixed at ambient temperature; the resulting mixture is then cast or extruded to form the foam. The foam can be prepared for subsequent use in a wound dressing or the like by any suitable method. For example, a suitable substrate, such as a plastic (e.g. in the form of a sheet, laminate or fibrous mat), paper, foil, or the like can be provided and coated with a medically acceptable adhesive. Such adhesives are generally well known to those skilled in the art. Then the reactant composition is poured directly onto the adhesive where the foam is formed. The foam can then be covered by a cover sheet if desired. The resulting composite which comprises the substrate, adhesive, and foam can be die cut and later used itself, or it can be used as part of an occlusive or semi-occlusive wound dressing.

To assist in contacting the skin and effecting the nociceptive system as herein described, preferably, the surface of the foam which contacts the skin is not glassy or polished but somewhat rough in texture. Moreover, the foam preferably has a plurality of cells that vary in regard to their average cell diameter. More preferably, cells of differing diameter are distributed substantially randomly throughout the composition. For example, the cell size can range from about 0.002 mm to about 3 mm, such as from about 0.01 mm to about 1 mm, and more typically from about 0.03 to about 0.06 mm. The foam composition will then assist in maintaining a moist seal appropriate to effectuate the inventive method. While many suitable compositions for use in the inventive method can be prepared as described above, a most preferred example of such composition for use in the present inventive method is POLYMEM™, marketed by Ferris Manufacturing Corporation. Further examples of suitable compositions are disclosed in U.S. Pat. Nos. 5,064,563 and 5,065,752, both of which are incorporated herein by reference.

For use in the inventive method, the composition is applied to any desired area of the skin. The exact area of application will depend on the desired result. Generally, the noxious response of nociceptors innervating the skin directly underlying the composition will be attenuated. Thus, for applications in which the noxious stimuli are largely epidermal, the composition can be applied to the surface of the skin directly covering the afflicted area. In this regard, the degree to which an individual neurite is affected by the presence of adjuvant is not critical. As mentioned, the termini of nociceptors are loosely arranged in networks, and normal nociceptive response potentiates an entire local network through positive feedback (e.g., via sensitization due to substance P, stimulation via histamines, etc.). When the ability of even a few nociceptor neurites to respond to noxious stimuli is attenuated, the capacity of an entire network within a discrete area to respond is dramatically reduced relative to its normal response capacity. Thus, the present inventive method effects an additive response impacting the entire region of the skin underlying the site of application.

Once affixed to the skin surface, a foam composition can adsorb moisture, such as exudate moisture from a wound, sweat, etc. In absorbing the moisture, the foam swells to conform to the surface contour so as to become electrochemically insulative to the surface of application, while at the same time holding moisture against the surface to keep that surface moist and to maximally permit the composition to contact the skin while decreasing the exposure to air. Where the foam composition is used on an open wound, it does not adhere to the wound and thus does not cause reinjury upon its removal from the wound. This is believed to be due to the liquid exchange and the maintenance of a moist environment about the wound.

Without being bound by any particular theory, the hydrophilic agent is believed to work in conjunction with the foam matrix to hold moisture at the surface of the skin. Thus, preferably the surface of skin to which the composition is applied is moist. This property facilitates electrical conductance through a fluid continuum between the nociceptor neurons and the foam composition, in turn affecting the Donnan equilibrium across the membranes of nociceptive neurons, hyperpolarizing them. Where the foam composition is applied to broken skin, this property also allows healing agents exuded by the wound to be concentrated and held at the wound surface. At the same time, the hydrophilic agent incorporated into the composition is believed to absorb fluid from any wound to assist thickening of the blood, i.e., it serves as a hemostat. The absorption of exudate by the hydrophilic agent, and the subsequent swelling of the agent results in the removal of inflammatory exudates and particles that would otherwise hinder tissue repair, cause scar formation, and stimulate nociceptors. Necrotic debris and bacteria are likewise removed as autolysis, i.e. chemical debridement is stimulated. Moreover, it is believed that the foam matrix serves as a capacitor to further effect the resting potential of the neurons. Thus, one aspect of the present invention involves altering the polarization of peripheral nociceptors by applying the aforementioned composition to the surface of the skin. By such manipulation, the neurons are less able to conduct electrochemical signals. Hence the ability of the nociceptors to respond to noxious stimuli, as well as to conduct both afferent and antidromal signals, is attenuated.

The effects of the present inventive method are not limited to interfering with nociceptive responses in the skin adjacent to the area on which the composition is applied. Indeed, the effects can be realized at sites distant from the area of application, such as contralateral sites and internal sites. Thus, for example, applying the composition to the skin surface can attenuate bruise formation deep to the surface (e.g., a bone bruise). For affecting nociceptors in joints (such as to treat arthritic or post operative swelling and/or pain), the composition is applied to the surface of the skin overlying the joint. Moreover, as mentioned, nociceptive neural innervation of the central nervous system effects a dermatomic summation or experience of noxious stimuli, reflecting the quasi-segmental organization of peripheral inputs. As such, the inventive method can attenuate the response of central neural pathways to nociceptive input from internal structures. Chiefly, by applying the composition to the skin, the activity of the nociceptors underlying the composition is attenuated or minimized. As such, the input received in the central nervous system lacks appreciable amount of stimulus from the dermal afferents. Due to the dermatomal summation within the spinal column, this attenuation of dermal nociceptive input is realized as an overall reduction in afferent input at the level of a given dermatome. In some applications, this effect can reduce or eliminate pain stemming from noxious stimuli deep to the surface of the skin. For example, Table 1 indicates some dermal application sites for effecting nociceptive input originating in various internal organs. Generally speaking, for interfering with dermatomic summation of signals, the area of skin within a given dermatome to which the composition is applied corresponds to the degree to which summation within the spinal column is affected. Thus, for a greater effect, more skin should be covered with the composition.

TABLE 1

| Nociceptor Terminal Origin | Site of Application |
| --- | --- |
| Upper mouth | Skin over the maxillary division of the trigeminal nerve |
| Lower mouth | Skin over the mandibular division of the trigeminal nerve |
| Lung and tracheo-bronchial tree | Skin over the anterior and posterior cutaneous divisions of spinal nerves C1 through T9 |
| Stomach | Skin over the anterior and posterior divisions of spinal nerves T4 through T10 |
| Esophagus | Skin over the anterior and posterior divisions of spinal nerves C6 through T5 |
| Small intestines | Skin over the anterior and posterior divisions of spinal nerves T9 through T12 |
| Large intestine/rectosigmoid | Skin over anterior and posterior divisions of spinal nerves T12 through S3 |
| Pelvic structures | Skin over the anterior and posterior divisions of spinal nerves T10 through S4 to their; skin over the pubic area anteriorly; the inner upper thigh area bilaterally and the sacral region posteriorly |

As mentioned, nociceptive input to the central nervous system can simultaneously stimulate other efferent termini within the central nervous system, leading to neurogenic swelling and pain distant from the situs of the initial noxious stimulus via antidromic conductance. Because the inventive method attenuates local nociceptor response to noxious stimuli as well as their ability to conduct signals, the present inventive method reduces or eliminates many neurogenic effects. Thus, application of the aforementioned compositions to the site of the noxious stimulus reduces the effect on other areas (e.g., skin on the contralateral side, joints, etc.). Furthermore, application of the aforementioned compositions to skin distant from the site of the noxious stimulus reduces the response of skin underlying the composition to antidromic stimulation.

By thus attenuating nociceptive response, the inventive method mediates several potentially therapeutic responses in the patient. The method functions well in mammals, and is applicable to human and non-human patients (e.g., cats, dogs, horses, pigs, cattle, etc.). As mentioned, both through the direct action of neuropeptides and indirectly (e.g., through the activities of cells responding to substance P), nociceptors mediate bruise formation in response to trauma. Thus, by attenuating the response of nociceptors to such noxious stimuli, the inventive method effectively treats (i.e., promote the healing of) traumatized tissue of a patient, for example, by attenuating the formation of bruises, inflammation, and swelling within such tissue. The method can be applied to treat many types of trauma to tissue, e.g., resulting from surgical or other therapeutic procedures, sports- or work-related injuries (for example, sprains, inflammation, etc.), accidental injuries (such as resulting, from blows, burns, laceration, etc.), and other types of trauma. In accordance with the inventive method, the composition can be applied to the skin at any time following the trauma. However, the composition preferably is applied as soon as possible following the trauma, to prevent and attenuate the tissue's response to the trauma.

Because, as mentioned, nociceptive neurons potentiate bruise formation, attenuating the response of nociceptors via the inventive method interferes with their ability to mediate bruise formation. Thus, in one aspect, the invention pertains to a method of attenuating or preventing the formation of a bruise in traumatized tissue involving the application of the aforementioned composition to the surface of the skin. Bruising can be attenuated in skin by applying the composition directly to skin over the area subjected to trauma in an amount and at a location sufficient to attenuate the formation of a bruise in the traumatized tissue.

Because, as mentioned, nociceptors mediate neurogenic inflammatory responses in patients subjected to noxious stimuli, attenuating the response of nociceptors to such noxious stimuli interferes with their ability to mediate neurogenic inflammatory responses. Thus, a further aspect of the invention is a method of attenuating neurogenic inflammation in a patient involving the application of the aforementioned composition to the surface of the skin in an amount and at a location sufficient to attenuate neurogenic inflammatory response in a patient. The method attenuates neurogenic inflammation regardless of its cause. Thus, the method can reduce or prevent inflammation due to noxious stimuli (e.g., burns, chemical irritants, pressure, wounding, etc.), allergies, or diseases (e.g., inflammatory diseases of the skin, such as acne, eczema, morphea, etc.). The method can attenuate neurogenic inflammation locally (e.g., by inhibiting the ability of a given nociceptor to directly or indirectly affect surrounding tissues or a local array of peripheral nociceptor termini, as described herein). Alternatively, the method can attenuate neurogenic inflammation due to antidromic response of peripheral nociceptor termini by more central stimulation (e.g., reflexive neurogenic responses, as described herein). The degree to which the method attenuates such neurogenic inflammation is sufficient to confer a therapeutic effect to the patient, and can range from a slight reduction in redness or swelling to the complete blocking of such symptoms.

A further use of the inventive method is in treating swelling. As mentioned, nociceptors mediate swelling in dermal and subdermal tissues. Thus, by attenuating the response of nociceptors, the present invention interferes with the ability of such neurons to stimulate each other and to release chemicals into the periphery which mediate swelling. As such, an aspect of the invention is a method of attenuating swelling in a patient via the application of the aforementioned composition to the surface of the skin in an amount and at a location sufficient to attenuate swelling in the patient. The method can reduce extant swelling or prevent swelling from occurring. The method can reduce swelling locally (e.g., in the skin underlying the area of composition application). Alternatively, as mentioned, the method can attenuate swelling in tissues deep to the skin (e.g., within joints) within the same dermatome of the area of skin to which the composition is applied.

A further use of the inventive method is in treating pain. As mentioned, in response to noxious stimuli, nociceptors transmit signals to central nervous system neurons in neural pathways associated with pain sensation. Thus, by attenuating the response of nociceptors to noxious stimuli, the present invention interferes with the ability of such neurons to inform the central nervous system of the noxious stimuli, thereby interfering with the neurophysiology as well as the sensation of pain. In physiological terms, the application of the aforementioned compositions to the surface of skin elevates the threshold of stimulation required to effect the spinal pathways implicated in pain sensation. As such, the inventive method elevates the threshold of pain. Viewed subjectively, the invention provides a method of reducing the sensation of pain in a patient via the application of the aforementioned composition to the surface of the skin in an amount and at a location sufficient to attenuate the sensation of pain in the patient. The method can reduce pain locally (e.g., in the skin underlying the area of composition application). Alternatively, as mentioned, the method can reduce pain in tissues deep to the skin within the same dermatome of the area of skin to which the composition is applied.

The following examples further illustrate the invention. Of course, as these examples are included for purely illustrative purposes, they should not be construed to limit the scope of the present invention in any respect.

EXAMPLE 1

This example demonstrates that the application of a composition comprising a hydrophilic foam substrate, a polymeric hydrophilic agent capable of absorbing water, and a wetting agent to the surface of the skin prevents the formation of a bruise in traumatized tissue.

A patient was subjected to a blow to her upper arm. Immediately thereafter, a patch consisting of POLYMEM™ was applied to the surface of the skin partially covering the traumatized area. Sixteen hours later, the arm was inspected, and it was observed that the skin surrounding the patch had darkened, indicating that a bruise had formed. The composition was removed, and visual inspection surprisingly revealed no discoloration of the skin underlying the patch. In fact, the bruise ended in a sharply delineated line, representing the boundary of the skin over which the composition had been applied. The patient was observed 48 hours later, which revealed that, while the bruised area had faded normally, no bruise had developed in the area underlying the composition. These results demonstrate that the inventive method prevents the formation of a bruise in traumatized tissue.

EXAMPLE 2

This example demonstrates that the application of a composition comprising a hydrophilic foam substrate, a polymeric hydrophilic agent capable of absorbing water, and a wetting agent to the surface of the skin prevents the formation of a bruise in traumatized tissue.

A device was constructed to deliver calibrated blows consistently by dropping a weight of about 1.8 kg, falling a distance of 30 cm with a contact area of 1 $cm^2$. Fourteen New Zealand White rabbits (2.75-3.00 kg) were anesthetized and subjected to blows to the gastrocnemius area of each of hind leg using the device. Following the procedure, one hind leg of each rabbit was immediately wrapped in a dressing consisting of POLYME™. To equalize pressure, the other leg was wrapped in a dressing consisting of an ACE bandage.

After 24 hours, and again at 48 hours, the legs were uncovered and examined. Bruises which had formed were graded between 1 (least severe) and 4 (most severe) by consensus of three researchers. The average value for the swelling in the POLYMEM™ treated legs 24 hours later was determined to be 0.71, while the average in the control legs was 3.29. This difference was subjected to analysis by a Paired T-Test, and the difference between the two average values was found to be very highly significant ($p<0.001$). The average swelling in the POLYME™ treated legs 48 hours later was 0.29, while the average in the untreated legs was 2.36. The T-Test determined that the difference between these two averages was very highly significant ($p<0.001$). These results demonstrate that the inventive method prevents the formation of a bruise in traumatized tissue.

EXAMPLE 3

This example demonstrates that the application of a composition comprising a hydrophilic foam substrate, a polymeric hydrophilic agent capable of absorbing water, and a wetting agent to the surface of the skin reduces the sensation of pain and attenuates swelling and bruising.

A 65-year-old male patient underwent arthroscopic surgery to remove a meniscus fragment from his right knee. After the surgery, the knee was dressed with a dressing consisting of POLYMEM™.

Following this treatment, the patient required crutches on only one occasion the day of surgery to assist in mobility; the day following the surgery, the patient was able to walk comfortably without orthotics. The patient did not experience significant post operative pain, and he was not given any pain medication.

The knee and surgical wound were examined on the day following surgery. The examination revealed only slight superficial swelling directly beneath the sites of incision. The incision appeared neat and uncomplicated, and the skin evinced no sign of bruising. Musculoskeletal examination revealed 100% range of motion in the right knee in flexion, extension, and rotation. Muscle tone was normal, and comparison of the circumference of both legs revealed no loss of muscle mass.

On the third day post-operation, the patient demonstrated complete mobility without discomfort. He was able to conduct his normal daily activities without the need for pain medication or orthotic assistance.

The result of this procedure is surprising given the normal course of recuperation following such surgery in persons of similar age, which usually requires substantial orthotic assistance and physical therapy. Indeed, the same individual underwent a similar operation about ten years previously on his left knee. Following that procedure, he experienced a prolonged healing process of about two months, including physical therapy.

EXAMPLE 4

This example demonstrates that the application of a composition comprising a hydrophilic foam substrate, a polymeric hydrophilic agent capable of absorbing water, and a wetting agent to the surface of the skin reduces the sensation of pain. 24 individuals suffering from chronic lower back pain who had not responded well to other therapies were identified. These individuals were treated for ten days by covering an area of their lower backs with a dressing consisting of POLYMEM™. After this ten day treatment, the individuals were again examined, and 21 of them reported significant attenuation of their symptoms during the study.

EXAMPLE 5

This example demonstrates that the application of a composition comprising a hydrophilic foam substrate, a polymeric hydrophilic agent capable of absorbing water, and a wetting agent to the surface of the skin attenuates neurogenic inflammation.

A young woman was diagnosed with morphea. Her symptoms included numerous lesions, characterized by areas of dry, nonviable skin, each surrounded by a border of raised, inflammatory tissue, spread across her back. One side of her back was covered with a dressing consisting of with POLYMEM™, and the other side was left untreated. After this treatment, the inflammatory borders were absent and the pathologic process appeared to be quiescent. In contrast, the untreated side continued to exhibit the characteristic lesions.

All of the references cited herein, including patents, patent applications, and publications, are hereby incorporated in their entireties by reference.

While this invention has been described with an emphasis upon preferred embodiments and illustrative and comparative examples, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of attenuating the formation of or reducing the severity of neurogenic bruising in a tissue of a patient, the method comprising applying a composition comprising a hydrophilic foam substrate and a hydrophilic agent to a portion of the surface of the skin of the patient in an amount and at a location sufficient to attenuate the formation of or reduce the severity of a neurogenic bruise in the tissue, wherein the bruising is associated with skin tissue other than a site of trauma.

2. The method of claim 1, wherein the entirety of the portion of skin is unbroken.

* * * * *